US009011438B2

(12) United States Patent
Steiner et al.

(10) Patent No.: US 9,011,438 B2
(45) Date of Patent: Apr. 21, 2015

(54) RADIOLUCENT ORTHOPEDIC FIXATION PLATE

(75) Inventors: Christian Steiner, Eisenach (CH);
Philippe Lehmann, Lamboing (CH);
Beat Knuchel, Ursenbach (CH);
Vinzenz Burgherr, Bern (CH)

(73) Assignee: Stryker Trauma SA (CH)

( * ) Notice: Subject to any disclaimer, the term of this patent is extended or adjusted under 35 U.S.C. 154(b) by 823 days.

(21) Appl. No.: 12/214,893

(22) Filed: Jun. 23, 2008

(65) Prior Publication Data
US 2009/0264883 A1 Oct. 22, 2009

(30) Foreign Application Priority Data
Apr. 18, 2008 (EP) .................................... 08154761

(51) Int. Cl.
A61F 5/04 (2006.01)
A61B 17/62 (2006.01)
A61B 17/00 (2006.01)

(52) U.S. Cl.
CPC ........ *A61B 17/62* (2013.01); *A61B 2017/00915* (2013.01)

(58) Field of Classification Search
USPC ........ 606/53–59; 206/533, 528, 538; 248/315
See application file for complete search history.

(56) References Cited

U.S. PATENT DOCUMENTS

| 2,055,024 A | 9/1936 | Bittner |
| 3,863,037 A | 1/1975 | Schindler et al. |
| 4,006,740 A | 2/1977 | Volkov et al. |
| 4,098,269 A * | 7/1978 | Judet ............................. 606/54 |
| 4,185,623 A | 1/1980 | Volkov et al. |
| 4,308,863 A | 1/1982 | Fischer |
| 4,365,624 A | 12/1982 | Jaquet et al. |
| 4,403,606 A * | 9/1983 | Woo et al. ...................... 606/70 |
| 4,450,834 A | 5/1984 | Fischer |
| 4,784,125 A | 11/1988 | Monticelli et al. |
| 4,889,111 A | 12/1989 | Ben-Dov |
| 5,062,844 A * | 11/1991 | Jamison et al. ................. 606/54 |
| 5,087,258 A | 2/1992 | Schewior |
| 5,496,319 A | 3/1996 | Allard et al. |
| 5,702,389 A | 12/1997 | Taylor et al. |
| 5,722,976 A * | 3/1998 | Brown ........................ 606/281 |
| 5,728,095 A | 3/1998 | Taylor et al. |

(Continued)

FOREIGN PATENT DOCUMENTS

DE 4421223 12/1995
FR 2576774 A1 8/1986

(Continued)

OTHER PUBLICATIONS

European Search Report, EP 08 15 7614.
(Continued)

*Primary Examiner* — Jerry Cumberledge
*Assistant Examiner* — Nicholas Plionis
(74) *Attorney, Agent, or Firm* — Lerner, David, Littenberg, Krumholz & Mentlik, LLP

(57) ABSTRACT

An orthopedic fixation plate comprises a plurality of cylindrical holes for attaching connectors of a external fixation system, wherein the fixation plate comprises two supporting elements around each orifice of a cylindrical hole wherein the supporting elements are connected with a sleeve and said supporting elements are also connected with a longitudinally oriented ring element arranged in a radial distance of said sleeve.

21 Claims, 1 Drawing Sheet

(56) References Cited

U.S. PATENT DOCUMENTS

| | | | |
|---|---|---|---|
| 5,779,703 A * | 7/1998 | Benoist | 606/54 |
| 5,891,143 A | 4/1999 | Taylor et al. | |
| 5,968,043 A | 10/1999 | Ross, Jr. et al. | |
| 5,971,984 A | 10/1999 | Taylor et al. | |
| 5,997,537 A | 12/1999 | Walulik | |
| 6,030,386 A | 2/2000 | Taylor et al. | |
| 6,391,250 B1 * | 5/2002 | Wolfsgruber et al. | 419/2 |
| 7,226,449 B2 | 6/2007 | Venturini et al. | |
| RE40,914 E | 9/2009 | Taylor et al. | |
| 8,257,353 B2 | 9/2012 | Wong et al. | |
| 2004/0073212 A1 | 4/2004 | Kim | |
| 2004/0167518 A1 | 8/2004 | Estrada, Jr. | |
| 2007/0049930 A1 * | 3/2007 | Hearn et al. | 606/56 |
| 2008/0221571 A1 * | 9/2008 | Daluiski et al. | 606/54 |

FOREIGN PATENT DOCUMENTS

| | | |
|---|---|---|
| RU | 2211000 | 8/2003 |
| WO | 92/14426 | 9/1992 |
| WO | 97/30650 | 8/1997 |
| WO | WO-97/30651 | 8/1997 |
| WO | 01/22892 | 4/2001 |
| WO | 2007075114 | 7/2007 |
| WO | WO 2007075114 A1 * | 7/2007 |

OTHER PUBLICATIONS

European Search Report, EP 08 15 4754.

Nanua et al., IEEE Transactions on Robotics and Automation, vol. 6, No. 4, pp. 438-444, Aug. 1990.

* cited by examiner

RADIOLUCENT ORTHOPEDIC FIXATION PLATE

BACKGROUND OF THE INVENTION

The invention relates to a radiolucent orthopedic fixation plate for use with an orthopedic external fixator.

External fixation systems are known in prior art from U.S. Pat. No. 5,062,844. They use orthopedic fixation plates having the shape of rings for use with additional fixator elements. The person skilled in the art knows such rings for example from the Ilizarov apparatus, which is also published as U.S. Pat. No. 4,615,338. Usually several rings are positioned around a limb, comprising e.g. a broken bone. The rings are interconnected by struts to accommodate elements such as posts etc. which are in connection with a wire being connected to a bony structure.

Such an entire system as well as the rings tend to hide the bone fracture during X-ray shooting. The fracture gap with the surrounding callus is an indicator for the doctor to interpret bone healing. When the doctor then shoots an X-ray image to judge the fracture healing, it is frequent that the fixator hides said fracture so that at least a second X-ray image is necessary for proper interpretation. This however increases the patient's radiation exposure, takes more time, is inconvenient and does not improve the quality of the x-ray itself.

Based on this prior art, it is known to use radiolucent fixation elements made from plastic or composite synthetic materials which are radiolucent. Such an external fixation device is known from WO 97/30651. These materials have the advantage of not masking the fracture area in X-ray images. These materials tend to creep over time, decreasing the tension within the fixation device, lowering the stiffness over time, which as a consequence may influence the bone healing. WO 97/30651 uses a core of a resin matrix reinforced with fibers, but the guiding length of the cylindrical holes for attaching connectors is quite short.

US 2004/0167518 suggests providing the rings in a radiolucent material as polycarbonate or carbon fiber. The rings are in cross-section double-T shaped having apertures or holes to provide the attachment points for the connectors in the thinner middle sections. Two separate beryllium rings are provided in the thicker T-ends of the fixator rings to increase stiffness while avoiding X-ray shading. These rings suffer the same problems as the former mentioned prior art.

SUMMARY OF THE INVENTION

The invention uses, inter alia, the insight that the fixation devices use long cylindrical holes as interface for attaching connectors. The inventors have realized that the portions of the fixation devices around such long holes are the main reason for the shielding effect leading to insufficient X-ray images.

The simple reduction of size of the fixation plate or reducing the length of these cylindrical holes does not lead to satisfactory results, since such devices then usually do not have sufficient strength. Furthermore, they no longer provide these relatively long cylindrical interfaces, which are useful or even necessary for providing an attachment portion for connectors to be fixed to such an external fixator.

Another aspect of the invention is the creation of a cost-effective strong external fixator element, which does not have the structural disadvantages of X-ray transparent elements.

Another aspect of the invention is also to provide an improved orthopedic fixation plate comprising a plurality of cylindrical holes for attaching connectors of an external fixation system. The fixation plate comprises two supporting elements around each orifice of a cylindrical hole wherein the supporting elements are connected with a sleeve and said supporting elements are also connected with a longitudinally oriented ring element arranged in a radial distance of said sleeve.

The supporting elements can be radially oriented flat ring plates which can comprise holes within which sleeves are mounted.

The longitudinally oriented ring element can be produced as a hollow cylinder element provided inside the connecting circle of the holes.

Preferably the thickness of each sleeve is about one-half of the thickness of the ring element.

The orthopedic fixation plate comprising the ring element, the supporting elements and the sleeves are preferably made in light metals, especially from the group comprising aluminum, titanium, magnesium.

An external fixation ring for treating bones according to one embodiment has first and second parallel plate elements having a plurality of holes for attaching connectors of an external fixation system. The holes of each plate are axially aligned and a cylindrical sleeve extends between the holes in the first and second plates to form a connection therebetween. The plates also connected by a cylindrical axially extending element arranged at a radial distance inwardly from the cylindrical sleeves. The first and second plates may be radially oriented flat rings. The flat ring plates comprise a plurality of circular holes within which the sleeves are mounted. The ring element may be a hollow cylinder element provided inside a circle contouring the centers of the holes. The thickness of each sleeve may be about one half of the thickness of the ring element. The first and second plates, the ring element and the sleeves are preferably made of light metals selected from the group consisting of aluminum, titanium or magnesium or combinations thereof. The first and second plates and the cylindrical sleeve extending therebetween may form a full circular ring, an elliptical ring, or a ring segment.

A ring for an external bone fixation system may include first and second plate elements axially spaced from each other by a cylindrically-shaped member connected to both plates. The first and second plate elements include a plurality of aligned holes with hollow sleeves extending between the first and second plate elements coaxially aligned with the holes. The sleeves preferably spaced radially outwardly from the cylindrically-shaped member. In the preferred embodiment the first and second plate elements are parallel. The first and second plate elements and the cylindrically-shaped member preferably form a U-shaped ring open to an outer circumference of the ring. The cylindrically-shaped member extends perpendicularly to the first and second parallel plate members. The hollow sleeves are cylindrical and the holes in the first and second plates are circular, the sleeves being connected to the first and second plates coaxially aligned with the holes. The sleeves are preferably welded to the first and second plates. The cylindrically-shaped member may be integrally formed as the inner circumference of the first and second plates. The first and second plates and the cylindrical-shaped member can be formed from a single metal sheet deformed to form the U-shaped ring. This metal sheet is made of a metal selected from the group consisting of aluminum, titanium and magnesium. The thickness of the metal sheets allows x-rays to pass therethrough so that the bone surrounded by the ring can be viewed on an x-ray photograph.

The hollow sleeves are made of the same metal as the metal sheet forming the first and second plates and have a thickness less than the sheet.

BRIEF DESCRIPTION OF THE DRAWINGS

Now the invention is more closely described with reference to the drawings and with the aid of exemplary embodiments.

DETAILED DESCRIPTION

Figure 1:
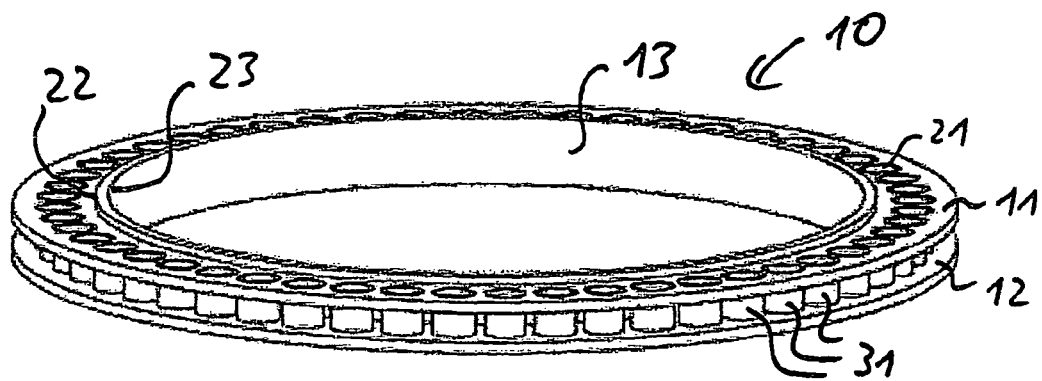
FIG. 1 shows a perspective view of an embodiment of an orthopedic fixation plate according to the present invention.

The embodiments are based inter alia on the insight that light weight metals are in principle non-radiolucent materials. However, such non-radiolucent materials as aluminum, titanium, magnesium and other light metals as well as alloys of these materials are nevertheless to a certain degree radiolucent if the wall material is thin enough. The device according to an embodiment of the invention is made of an aluminum alloy wherein the mean value of the cross section, independent of its direction, is sufficiently radiolucent to view the bone behind the device on an X-ray photo.

To achieve such a structure with strong geometrical properties in all directions and a mean cross section that is thin enough, multiple parts of thin aluminum profiles are put together, especially welded together. Although aluminum profiles are mentioned in this description, it is clear that use of other light weight metals is contemplated. Light metals are metals of low atomic weight. The cutoff between light metals and heavy metals varies and can be defined to be a density of 4.5 g/cm$^3$, light metals being metals having a lower density. Alkali metals, earth alkaline metals as well as transition metals of the third group (Sc, Y) as well as fourth group titanium (Ti) and aluminum are considered light metals. Additional metals up to nickel are often included as well. Metals heavier than nickel are usually called heavy metals.

The orthopedic fixation plate 10 uses a ring profile 13 with an open U-shape having free ends 11 and 12. Alone such a shape has no strong mechanical properties especially if loaded with torsion. The ring profile is nevertheless named a plate since the profile is used as is a conventional plate.

Multiple thin tubes 31 are connected along the circumference to achieve mechanical properties. These thin tubes 31 also form the long cylindrical holes 21 for modular connections and can absorb strong loads due to the profiles 11 and 12 strengthening the plate at the upper and lower side.

As mentioned above the material to be used can be aluminum, titanium, magnesium or other light metals. It is also possible to use alloys of these materials.

It is possible to build an adequate structure from single elements by using a laser-sinter-process and a metal powder.

FIG. 1 shows a perspective view of a preferred embodiment of the invention representing a fixation plate or ring 10. FIG. 1 is a perspective view, angular from the top. The fixation plate or ring 10 comprises an inner ring-shaped profile 13 to be positioned around a limb of the patient. The ring-shaped profile 13 has a hollow cylindrical form extending in the longitudinal direction of said limb to be positioned inside the ring 13. The longitudinal direction of limb to be positioned is preferably the central axis of symmetry of the ring 13.

The ring 13 comprises a radially oriented upper plate 11 and a radially oriented lower plate 12. Both ring-shaped plates 11 and 12 are spaced in a longitudinal distance from each other along a central axis of the ring and are congruent in a top view along said longitudinal axis of the limb to be positioned. The ring plates 11 and 12 comprise a plurality of holes 21 oriented perpendicular to the central axis of symmetry of the plates 11 and 12. There can be e.g. fifty-two holes 21 as in FIG. 1 or a greater or smaller number, which also depends on the diameter of the orthopedic plate 10, i.e. the diameter of the inner ring 13. Fifty-two holes 21 are arranged in a mutual annular distance of 6 degree 55$^5$/$_{13}$ minutes. This angle of course depends on the number of regularly angular spaced holes 21.

At the inner edges 22 and 42 of the plates 11 and 12 they are contacting the stabilizing hollow cylinder ring 13. The wording "cylinder" relates to the fact that the cylinder ring 13 has a substantial dimension in parallel to the longitudinal axis of the plate 10. At the upper and lower ends of the ring 13, said edges 22 and 42 are affixed to the ring 13. The embodiment according to FIG. 1 comprises a shoulder 23 extending beyond the upper and lower surface of the rings 11 and 12, respectively. In other embodiments (not shown) the surface of the rings 11 and 12 can be flush with the free edges of the inner ring 13.

Two corresponding holes 21 in the upper and lower plates 11 and 12 are oriented in such a way, that they have a common axis. The common axis is preferably parallel to the above mentioned longitudinal axis of the device 10. Existence of this common axis for each pair of holes 21 signifies that such two holes 21 from plates 11 and 12 are associated with each other and this allows the introduction of hollow sleeves 31 into each such pair of holes 21. In the preferred embodiment the hollow sleeves 31 do not extend beyond the upper or lower surface of the upper and lower plates 11 and 12, respectively.

In other words, each hole 21 has therefore orifices at the surface of the plates 11 and 12. These orifices are thus forming the end surfaces for connector elements which are introduced into one or more of the holes 21. The area of the corresponding orifices are connected on one hand by sleeve 31 and on the other hand by inner ring 13. It would therefore also be possible, in a less preferred embodiment, to replace the inner ring 13 by an outer ring. The plates 11 and 12 are also supporting elements, since they create the connection portion for the sleeves 31.

Figure 2:
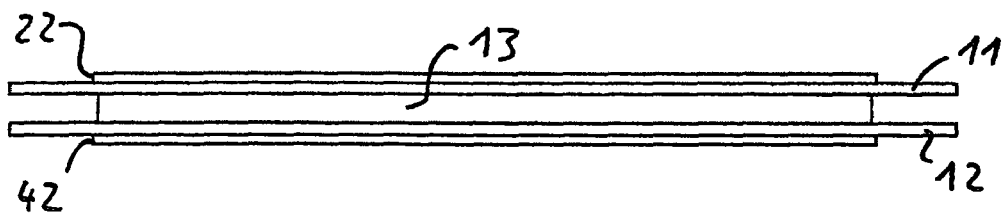
FIG. 2 shows a lateral view of the ring portions of the orthopedic fixation plate according to FIG. 1 without the guiding sleeves.
Figure 3:
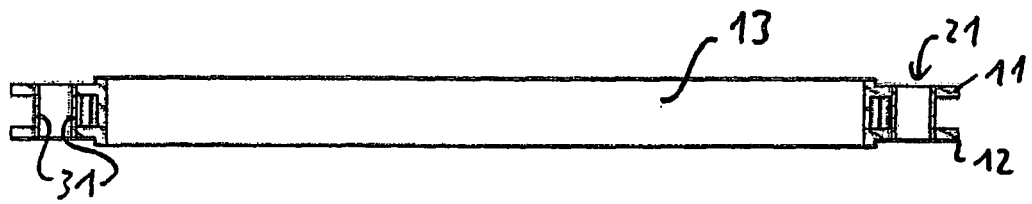
FIG. 3 shows a sectional view of the orthopedic fixation plate according to another embodiment according to the invention.

FIG. 2 shows a lateral view of the ring portions 11 and 12 of the orthopedic fixation plate according to FIG. 1 without the guiding sleeves 31. This embodiment is based on the representation of FIG. 1 wherein the guiding sleeves 31 are separate parts, attached to the ring plates 11 and 12 attached at the inner ring 13. However, as it is shown in FIG. 3 representing a section view of an orthopedic fixation plate according to another embodiment of the invention as well as in FIG. 4 being a detailed view of the external orthopedic fixation plate or ring according to FIG. 3, it is possible to provide the inner ring 13 as well as the plates 11 and 12 as a unitary element in one piece. Separate sleeves are then introduced into corresponding holes 21 in the plates 11 and 12.

Figure 4:
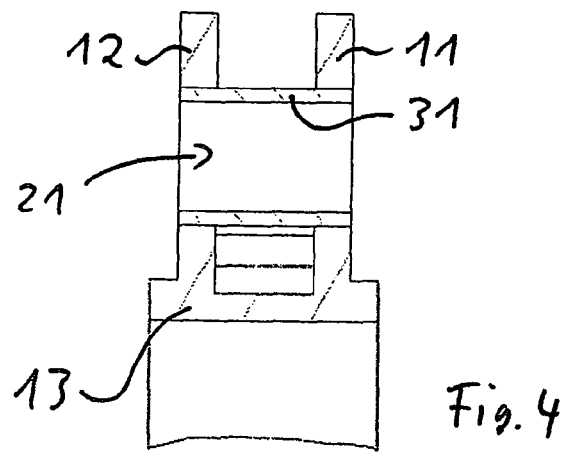
FIG. 4 shows a detailed view of the orthopedic fixation plate according to FIG. 3.

It can be seen from the detailed view of FIG. 4 that the use of plates 11 and 12 together with the ring 13 as well as sleeves 31 create a number of cavities within the enveloping structure of the fixation plate. These cavities can be open as between the free ends of the plates 11 and 12 or surrounded at a plurality of sides as between a sleeve 31 and the inner ring 13. In every direction of observation, i.e. in every possible direction an X-ray imaging device may use, the total material thickness of plates 11, 12, 13, 31 is thinner than the thickness of a conventional device providing the same guiding length for the interface surface for attaching connectors for e.g. struts or Kuerschner wires of an external fixation system.

It is noted that this advantage can be obtained if plates 11, 12 and ring 13 are made from one piece or if plates 11 and 12 are welded to ring 13. It is emphasized that the term embodiment in the description does not mean that only the elements described with respect to the respective external fixation plate are subject of the invention. In particular, these are also combinations of the characteristics described in objects of the various figures.

The inner ring 13 is shown as a closed ring. In other embodiments of the invention the ring 13 and plates 11 and 12 can comprise a partial ring segment. The "ring" can be an angle bracket or a ring segment.

Beside the use of separate sleeves 31 for every pair of holes 21 on plates 11 and 12, it is possible to provide a plurality of shaped structures to be attached with one another generating the surfaces of the sleeves 31 of the shown embodiments. The relevant advantage of both embodiments is based on the insight that an attachment connector can be fixed with sufficient strength if the guiding surface is long enough, independent of the thickness of the material surrounding the hole 21 between the end openings of the sleeve 31 or the shaped structure. It is also possible that the ring plates 11 and 12 themselves create the holes 21 and the sleeves 31 are attached between the ring plates 11 and 12, preferably introduced in recessed grooves in the plates 11 and 12 surrounding each hole 21. Within this description, the shaped parts surrounding a hole 21 are also named sleeves as are the separate sleeve 31 of FIGS. 1 and 4. Such sleeve forming profile parts can also be only a frame surrounding the hole 21. Preferably the thickness of the hollow sleeve 31 or of each shape profile portion surrounding the hole is about half the thickness of the ring 31 as can be seen in FIG. 4.

The holes 21 are arranged on a connecting circle portion, wherein the wording circle is used independent of the form of the fixation plate (ring, ellipse, L-bracket etc.).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A radiolucent orthopedic fixation plate comprising:
a cylindrical ring having an outer circumferential surface, axially spaced planar top and bottom surfaces and central axis; and
first and second annular plates extending radially outwardly from the cylindrical ring top and bottom surfaces, each plate extending in a direction transverse to the central axis forming an open space between the first and second plates;
wherein the first and second plates comprise a plurality of aligned cylindrical holes for attaching connectors of an external fixation system;
wherein each cylindrical hole of the first plate is connected with a corresponding cylindrical hole of the second plate through a tubular sleeve extending throughout said open space, the tubular sleeve having first and second ends fixedly respectively coupled to the first and second plates;
wherein the tubular sleeve intersects said open space to form a hollow space within the tubular sleeve being fully separated from said open space; and
wherein the outer circumferential surface of the cylindrical ring is spaced radially inwardly a distance from each sleeve in a direction transverse to the central axis such that said open space extends between each said sleeve and said outer circumferential surface.

2. The orthopedic fixation plate according to claim 1, wherein the first and second plates are planar.

3. The orthopedic fixation plate according to claim 1, wherein the cylindrical ring is a hollow cylinder and is located radially inwardly in a direction transverse to the central axis of a circle connecting center points of the holes of the first and second plates.

4. The orthopedic fixation plate according to claim 1, wherein the thickness of each sleeve is about one half of the radial thickness of the cylindrical ring.

5. The orthopedic fixation plate according to claim 1, wherein the cylindrical ring, the first and second plates and the sleeves are made from metals having a density less than 4.5 g/cm$^3$.

6. The orthopedic fixation plate according to claim 5, wherein the cylindrical ring, the first and second plates and the tubular sleeves are made from a metal selected from the group consisting of aluminum, titanium, and magnesium.

7. The orthopedic fixation plate of claim wherein the cylindrical ring has axially spaced planar end surfaces extending perpendicular to the central axis with the first and second plates located intermediate the cylindrical ring end surfaces and extending perpendicular to the central axis.

8. A radiolucent orthopedic fixation plate comprising:
a cylindrical ring extending axially about a central axis and defining an outer circumferential surface;
first and second annular plates mounted on the cylindrical ring, each plate extending transversely to the cylindrical ring central axis and spaced axially with respect to the cylindrical ring central axis to form a cavity between the first and second plates, the first and second plates each having a plurality of holes, the holes on the first plate aligned with the holes on the second plate when the first and second plates are mounted on the cylindrical ring; and
a plurality of tubular sleeves each connecting an aligned pair of the plurality of holes in the first and second plates, the sleeves extending through the cavity between the first and second plates and fixedly attached to the first and second plates, the aligned holes and sleeves are radially outwardly spaced in a direction transverse to the cylindrical ring central axis a distance from the outer circumferential surface of the cylindrical ring to form an open space between the cylindrical ring and the sleeves.

9. The orthopedic fixation plate according to claim 8, wherein the first and second plates are planar.

10. The orthopedic fixation plate according to claim 9, wherein the cylindrical ring is a hollow cylinder element having the central axis and is located radially inwardly in a direction transverse to the central axis of a circle connecting center points of the aligned holes of the first and second plates.

11. A radiolucent orthopedic fixation plate comprising:
a cylindrical ring defining an outer circumferential surface extending axially about a central axis, the cylindrical ring having an upper surface and a lower surface;
first and second plates extending from the cylindrical ring in an axially spaced relationship;

the first and second plates extending radially outwardly in a direction transverse to the central axis and forming an open space defined between the first and second plates and the outer circumferential surface of the cylindrical ring;

wherein the first and second plates comprise a plurality of aligned cylindrical holes for attaching connectors of an external fixation system; and a plurality of tubular sleeves each having a first end and a second end, each sleeve defining an outer surface and extending throughout said open space;

wherein each aligned cylindrical hole of the first plate is connected to a corresponding aligned cylindrical hole of the second plate by the one of the tubular sleeves extending throughout said open space, the first end of each tubular sleeve fixedly attached to the first plate and the second end of each sleeve fixedly attached to the second plate;

wherein each tubular sleeve intersects said open space to form a hollow space within the tubular sleeve being fully separated from said open space; and wherein the cylindrical ring outer circumferential surface is spaced at a radial distance toward the central axis from each tubular sleeve outer surface in a direction transverse to the central axis such that said open space extends between the cylindrical ring and tubular sleeve outer surfaces.

12. The ring as set forth in claim 11 wherein the first and second plates are parallel.

13. The ring as set forth in claim 12 wherein the first and second plates and the outer circumferential surface form a U-shaped ring open in a radially outward direction from the central axis of the cylindrical ring.

14. The ring as set forth in claim 13 wherein the cylindrical ring outer circumferential surface extends perpendicularly to the first and second parallel plates.

15. The ring as set forth in claim 14 wherein the outer circumferential surface is integral with an inner circumference of the first and second plates.

16. The ring as set forth in claim 15 wherein the first and second plates and the cylindrical ring are formed from a single metal sheet deformed to form the U-shaped ring.

17. The ring as set forth in claim 16 wherein the metal sheet is made of a metal selected from the group consisting of aluminum, titanium and magnesium.

18. The ring as set forth in claim 17 wherein the thickness of the metal sheet allows x-rays to pass therethrough so that a bone surrounded by the fixation plate can be viewed on an x-ray photograph.

19. The ring as set forth in claim 18 wherein the tubular sleeves are made of the same metal as the metal sheet forming the first and second plates and the cylindrical ring and have a thickness less than the sheet.

20. The ring as set forth in claim 11 wherein the tubular sleeves are cylindrical and the holes in the first and second plates are circular.

21. The ring as set forth in claim 20 wherein the tubular sleeves are fixedly attached to the first and second plates by a weld.

* * * * *

UNITED STATES PATENT AND TRADEMARK OFFICE
CERTIFICATE OF CORRECTION

Page 1 of 1

PATENT NO. : 9,011,438 B2
APPLICATION NO. : 12/214893
DATED : April 21, 2015
INVENTOR(S) : Christian Steiner et al.

It is certified that error appears in the above-identified patent and that said Letters Patent is hereby corrected as shown below:

Claims

Column 5, line 52, Claim 1 after "and" (second occurrence), insert -- a --.
Column 6, line 28, Claim 7 after "claim", insert -- 1 --.

Signed and Sealed this
Ninth Day of February, 2016

Michelle K. Lee
*Director of the United States Patent and Trademark Office*